United States Patent [19]

Segers

[11] Patent Number: Plant 7,253

[45] Date of Patent: Jun. 26, 1990

[54] GERBERA PLANT NAMED "EXTASE"

[75] Inventor: Th. A. Segers, Hoofddorp, Netherlands

[73] Assignee: Twyford Plant Laboratories, Inc., Santa Paula, Calif.

[21] Appl. No.: 316,910

[22] Filed: Feb. 28, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Townsend and Townsend

[57] ABSTRACT

An original variety of Gerbera plant distinguished by its pink outer petals and inner petals, its ability to grow vigorously and flower profusely during the spring, mid-season, and fall blooming periods as well as blooming in the winter in the greenhouse.

1 Drawing Sheet

BACKGROUND OF THE PLANT

This Gerbera (*Gerbera jamesonii*) variety, named 'Extase', originated as a seedling at Rijsenhout, and resulted from the crossing in March of 1981 of 77-224 as the seed parent and the pollen parent identified as 78-822, taken from my collection of gerbera maintained for breeding purposes at Rysenhout, the Netherlands. My objective in making the crossing being to develop new Gerbera varieties having blooms of good quality and excellent color on strong plants having good winter production in my greenhouses. This plant was selected from the seedlings resulting from the above crossing because of its extraordinary flower coloration of pink, its year-round production, and its vigorous and strong growth habit. The characteristics embracing the above objectives along with other desirable improvements as set forth below distinguish this new plant from its parents as well as from all other varieties of which I am aware.

The varieties thought to be most similar are 'Marleen', 'Gratia' and 'Pamela'. 'Extase' is distinguished from 'Marleen' by a different color and semi-double flowerhead. 'Extase' is distinguished from 'Gratia' by its color being pinker and having wider florets. 'Extase' is distinguished from 'Pamela' by its color being pinker and having more semi-double flowerhead.

Asexual propagation of this selected plant was carried on under my direction at Rysenhout by cuttings and further by means of tissue culture at Naaldwijk, the Netherlands, through several successive generations which clearly demonstrated that the novel characteristics of its blooming and growth habits appear to be firmly fixed and would remain true from generation to generation.

The following is a detailed description of my new gerbera plant based upon observations of greenhouse plants grown at Naaldwijk, Netherlands, the color designations being according to the R.H.S. Colour Chart published by the Royal Horticultural Society of London, England.

DESCRIPTION OF THE DRAWING

This new variety is illustrated by the accompanying photographic drawing (FIG. 1) which shows its bloom in full color, with such colors of the photograph being as true to those of the plant as can be reasonably obtained from conventional professional photographic procedures.

DESCRIPTION OF THE PLANT

Figure 1:
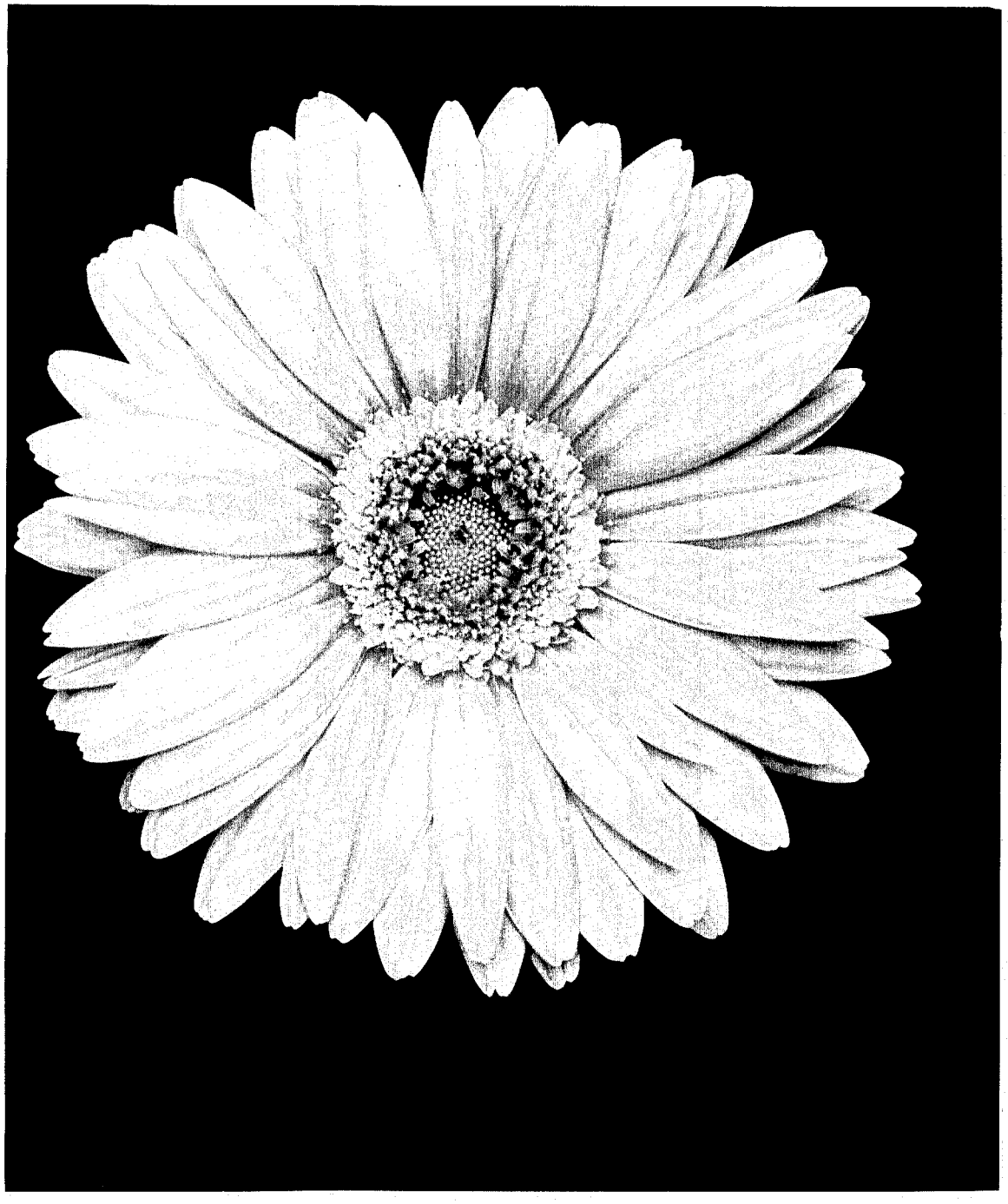

Leaf length: Medium.
Leaf width: Medium.
Leaf blade thickness: Thick.
Leaf blade blistering: Weak.
Leaf blade pubescence on upper side mid-rib excluded: Medium.
Leaf blade depth of incisions on basal part: Deep.
Leaf blade depth of incisions on the central third: Medium.
Leaf blade depth of incisions on distal part: Shallow.
Leaf blade color of upper side: Medium Green R.H.S. 137 B.
Leaf blade glossiness of upper side: Strong.
Leaf blade angle of apex: Obtuse.
Leaf blade shape of apex: Rounded.
Leaf blade margin of lobes: Sinuate.
Leaf blade extensions of margin: Small.
Petiole length: Medium.
Petiole anthocyanin coloration: Present.
Petiole intensity of anthocyanin coloration: Medium.

DESCRIPTION OF THE FLOWER

Peduncle length: Medium.
Peduncle cross section: Elliptic.
Peduncle tendency to fasciation: Present.
Peduncle thickness: Medium.
Peduncle strength: Strong.
Peduncle pubescence: Medium.
Peduncle color: Medium Green R.H.S. 144 A.
Peduncle anthocyanin color at base: Present.
Peduncle intensity of anthocyanin coloration at base: Weak.
Peduncle anthocyanin coloration at top: Absent.
Peduncle involucral bracts: Absent.
Flower head type: Semi-double.
Flower head diameter: Medium.
Flower head height from point of attachment of involucre to top of flower head: Medium.
Flower head height of involucre: Medium.
Flower head diameter of involucre: Medium.
Flower head number of involucral bracts: Medium.
Flower head longitudinal axis of bracts of inner rows of involucre: Reflexing, weak.
Flower head anthocyanin coloration at top of inner involucral bracts: Absent.

Flower head intensity of anthocyanin coloration at top of inner involucral bracts: N/A.
Flower head pubescence of involucre: Medium.
Flower head number of ray florets of outer rows: Medium.
Flower head shape of ray florets of out row: Narrow elliptic.
Ray floret longitudinal axis of rays of outer row: Reflexing.
Ray floret longitudinal axis of rays of inner row (normally developed ray florets): Straight to slightly reflexing.
Female floret longitudinal axis of ray (outer ray florets excluded — semi-double or double varieties only): Straight, top sometimes reflexing.
Male floret longitudinal axis of ray (semi-double or double varieties only): Straight, top reflexing.
Outer ray floret cross section of ray: Flat.
Outer ray floret length: Medium.
Outer ray floret width: Broad.
Outer ray floret longitudinal folding: Strong.
Outer ray floret angle of apex: Right angle.
Outer ray floret shape of apex: Rounded.
Outer ray floret incisions of apex: Present.
Outer ray floret number of incisions: Two.
Outer ray floret depth of incisions: Medium.
Outer ray floret length of free petals: Shallow.
Outer ray floret color of inner side:

| Description | Remarks |
|---|---|
| RHS 54C-D | Pink like RHS 54C-D, but strongly diffused and spread irregularly; toward top somewhat lighter and top edge is creamy white |

Outer ray floret distribution of the color on the inner side: Lighter towards the top.
Outer ray floret edge of different color: Absent.
Outer ray floret striation: Absent.
Outer ray floret color of outer side:

| Description | Remarks |
|---|---|
| RHS 2C<br>RHS 55C-D | Yellow-green like RHS 2C with irregular pinkish tint like RHS 55C-D |

Outer ray floret claw spot: Present.
Disc diameter (single or semi-double varieties only): Medium.
Disc main color before flowering of disc florets (single or semi-double varieties only): Green R.H.S. 145 A.
Disc main color of perianth lobes of female flowers: Pink, R.H.S. 54C-D.
Disc main color of perianth lobes of male flowers: Pink, dark pink, dentated white R.H.S. 54 D.

DESCRIPTION OF REPRODUCTION ORGANS

Style main color of distal part: White R.H.S. 11 D.
Stigma main color: Yellow, light yellow R.H.S. 2 D.
Anthers main color: Dark Yellow R.H.S. 16 A.
Anthers color of top relative to other parts: Darker.
Anthers longitudinal stripes: Present.
Pappus main color: Yellow R.H.S. 145 A.
Pappus color of top relative to other parts: Identical.
Pappus level of top relative to closed disc florets: Above.

I claim:

1. The new distinct variety of Gerbera plant herein described and illustrated and identified by the characteristics enumerated above.

* * * * *